United States Patent
Zhao et al.

(10) Patent No.: US 12,371,742 B2
(45) Date of Patent: Jul. 29, 2025

(54) METHOD FOR SEQUENCING POLYNUCLEOTIDES

(71) Applicant: Qingdao MGI Tech Co., Ltd., Qingdao (CN)

(72) Inventors: Jie Zhao, Shenzhen (CN); Sha Liao, Shenzhen (CN); Wenwei Zhang, Shenzhen (CN); Ao Chen, Shenzhen (CN); Chongjun Xu, Shenzhen (CN); Defeng Fu, Shenzhen (CN)

(73) Assignee: Qingdao MGI Tech Co., Ltd., Qingdao (CN)

( * ) Notice: Subject to any disclaimer, the term of this patent is extended or adjusted under 35 U.S.C. 154(b) by 1082 days.

(21) Appl. No.: 17/292,400

(22) PCT Filed: Nov. 7, 2018

(86) PCT No.: PCT/CN2018/114281
§ 371 (c)(1),
(2) Date: May 7, 2021

(87) PCT Pub. No.: WO2020/093261
PCT Pub. Date: May 14, 2020

(65) Prior Publication Data
US 2022/0010370 A1    Jan. 13, 2022

(51) Int. Cl.
*C12Q 1/6869* (2018.01)
(52) U.S. Cl.
CPC .................................. *C12Q 1/6869* (2013.01)
(58) Field of Classification Search
None
See application file for complete search history.

(56) References Cited

U.S. PATENT DOCUMENTS

| | | | |
|---|---|---|---|
| 5,436,130 | A | 7/1995 | Mathies et al. |
| 9,453,258 | B2 * | 9/2016 | Kain ............... C12Q 1/6874 |
| 2013/0045872 | A1 | 2/2013 | Zhou et al. |
| 2014/0178878 | A1 | 6/2014 | Müller et al. |
| 2019/0330693 | A1 | 10/2019 | Liu et al. |

FOREIGN PATENT DOCUMENTS

| | | |
|---|---|---|
| CN | 102858995 A | 1/2013 |
| CN | 103502474 A | 1/2014 |
| CN | 103602719 A | 2/2014 |
| WO | 00/58707 A1 | 10/2000 |
| WO | 2013/044018 A1 | 3/2013 |
| WO | 2014130388 A1 | 8/2014 |
| WO | 2018/129214 A1 | 7/2018 |
| WO | 2018/165099 A1 | 9/2018 |

OTHER PUBLICATIONS

Supplementary European Search Report issued in corresponding European Application No. 18939391.1 dated Jul. 11, 2022, 1 page.
International Search Report issued in corresponding International Application No. PCT/CN2018/114281 dated Feb. 15, 2019, 2 pages.

* cited by examiner

*Primary Examiner* — Robert J Yamasaki
(74) *Attorney, Agent, or Firm* — Kilpatrick Townsend & Stockton LLP

(57) ABSTRACT

The present invention provides a method for sequencing polynucleotides. Sequential incorporation of different nucleotides is detected by using the same light emitting signal, thereby achieving the determination of polynucleotide sequences.

9 Claims, 3 Drawing Sheets

METHOD FOR SEQUENCING POLYNUCLEOTIDES

CROSS-REFERENCE TO RELATED APPLICATIONS

This application is a national stage entry under 35 U.S.C. § 371 of International Application No. PCT/CN2018/114281, filed Nov. 7, 2018, the entire contents of which are incorporated by reference in their entireties for all purposes herein.

TECHNICAL FIELD

The present invention relates to a method for sequencing a polynucleotide, wherein sequential incorporation of different nucleotides is detected by the same luminescence signal, thereby achieving the sequencing of the polynucleotide.

BACKGROUND ART

In 1977, Sanger invented the dideoxy chain-termination sequencing method that is a representative of the first-generation sequencing technology. In 2001, relying on the first-generation sequencing technology, the human genome draft was completed. The Sanger sequencing method has the characteristics of simple experimental operation, intuitive and accurate results and short experimental period, and has a wide range of applications in clinical gene mutation detection and genotyping that require high timeliness of detection results. However, the Sanger sequencing method has low throughput and high cost, which limit its application in large-scale gene sequencing.

In order to overcome the shortcomings of the Sanger sequencing method, the second-generation of sequencing technology came into being. Compared with the first-generation sequencing technology, the second-generation sequencing technology has the advantages of large throughput, low cost, and high-degree of automation, and is suitable for large-scale sequencing. The currently developed second-generation sequencing technology mainly involves sequencing by ligation (SBL) technology and sequencing by synthesis (SBS) technology. Typical examples of these sequencing technologies include the Roche 454 sequencing method, the SOLiD sequencing method developed by Applied Biosystems, the combined probe anchor ligation method (cPAL) independently developed by Complete Genomics, and the combined probe anchor synthesis method (cPAS) developed by BGI, the Illumina sequencing method jointly developed by Illumina and Solexa Technology, etc. Sequencing detection methods mainly include electrochemical methods and optical signal detection methods, among which the more mainstream detection method is optical signal detection. In order to realize the identification and differentiation of 4 kinds of bases (A, T/U, C and G), 4 kinds of fluorescent dyes are needed to label 4 kinds of bases respectively. At present, there are also reports using two fluorescent dyes to label four bases, and the identification and differentiation of four bases can be achieved through different combinations of two fluorescent dyes. The Roche 454 sequencing method utilizes the principle of autofluorescence in which the pyrophosphate generated by the dNTP synthesis to the sequence to be tested is converted into ATP, the generated ATP and luciferase together oxidize luciferin to produce fluorescence, and the presence and strength of the fluorescence signal are detected to distinguish the 4 kinds of bases and the number of synthesized bases. Due to the hardware requirements of the second-generation sequencing technology, the instruments are generally relatively large, which is not conducive to carrying and handling.

At present, the sequencing technology has developed to the third-generation, which overcomes the disadvantages of large instruments of the second-generation sequencing technology. For example, the Oxford Nanopore sequencer can even be carried to space to perform sequencing experiment because the size of its sequencer is greatly reduced due to its different sequencing principles. However, the high error rate of the current third-generation sequencing technology limits its large-scale promotion.

The sequencers developed by Illumina, Complete Genomics and BGI, for examples, use four kinds of fluorescent dyes to label four kinds of bases, and laser excitation is used to collect different fluorescent signals to distinguish different bases. See, for example, Sara Goodwin, John D. McPherson and W. Richard McCombie, Coming of age: ten years of next-generation sequencing technologies. *Nature reviews*, 2016, 17: 333-351c.

The NextSeq sequencing system and Mini-Seq sequencing system developed by Illumina, as well as the BGISEQ-50 sequencing system of BGI, use two fluorescent dyes to label four kinds of bases, and use different combinations of two fluorescent dyes to achieve the identification and differentiation of four kinds of bases. For example, by labeling base A with the first fluorescent dye, labeling base G with the second fluorescent dye, labeling base C with the first and second fluorescent dyes at the same time, and not labeling base T, the four kinds of bases can be distinguished. See, for example, U.S. Pat. No. 9,453,258 B2.

In the Roche 454 sequencing method, when each kind of deoxyribonucleotide (dNTP) is passed sequentially, if the dNTP can be paired with the sequence to be tested, the pyrophosphate will be released after the dNTP is synthesized, and the pyrophosphate will interact with the ATP sulfurylase in the sequencing reaction system to generate ATP, and the generated ATP together with luciferase in the system oxidizes luciferin to emit fluorescence, and the fluorescence signal is captured by the detector and converted into a sequencing result by computer analysis. See, for example, Martin Kircher and Janet Kelso. High-throughput DNA sequencing—concepts and limitations. *Bioessays*, 2010, 32: 524-536.

The Ion torrent sequencing system is similar to the Roche 454 sequencing method, in which each kind of deoxyribonucleotide (dNTP) is passed sequentially, if the dNTP can be paired with the sequence to be tested, hydrogen ions will be released after the dNTP is synthesized, and the generated hydrogen ions will change the pH value of the reaction system, the electrical components integrated on the sequencing chip convert the pH value changes into electrical signals and transmit them to the computer, and they are converted by computer analysis into sequencing results. See, for example, Sara Goodwin, John D. McPherson and W. Richard McCombie, Coming of age: ten years of next-generation sequencing technologies. *Nature reviews*, 2016, 17: 333-351.

These technologies have the following shortcomings:

1. Four kinds of fluorescent dyes are used to label 4 kinds of bases. In order to distinguish different fluorescent signals, the sequencing equipment is equipped with at least 2 kinds of monochromatic excitation light sources and 2 cameras, which leads to the expensive manufacturing cost and huge volume of the sequencing device.

2. Compared with the use of 4 kinds of fluorescent dyes, using 2 kinds of fluorescent dyes to label 4 kinds of bases can reduce the equipment manufacturing cost and the equipment volume, but it is proved by experiments that because one dNTP is labeled with two kinds of fluorescence in the scheme and two kinds of fluorescence are excited by laser at the same time, the template state becomes worse as the length of sequencing increases (for the existing second-generation sequencing technologies, regardless of the principles, they all have problem that the quality of sequencing becomes worse as the read length increases), the resultant unbalanced excitation of the two label fluorescences (one of the fluorescences has an intensity significantly higher than that of the other) makes the dNTP signal of such fused fluorescence tends to mix with the signal of single fluorescence label, which leads to that different dNTPs cannot be distinguished, so that the quality of sequencing is significantly lower than that of the detection method using 4 fluorescent dyes.

3. For all detection methods that uses 4 or 2 kinds of fluorescent dyes to label 4 kinds of bases, there may be signal interference between different fluorescences, which affects the quality of sequencing.

4. For the Roche sequencing method and the Ion torrent sequencing method, although they do not need excitation light source and camera, etc., the deoxyribonucleotides used therein are in natural state, so that when the sequence to be tested has an arrangement of repeated bases, such as 5'-AT-TTG-3', compared with a sequence with base arrangement of 5'-ATG-3', they can only be distinguished by signal strengths (theoretically, the signal value of the sequence 5'-ATTTG-3' is about 3 times that of the sequence 5'-ATG-3'). However, such discrimination method is greatly interfered by sequencing conditions and is not easy to control, especially when the read length is long, it is difficult to distinguish the two sequences.

Therefore, there is still a need for a sequencing method with lower cost and better effect in the art.

CONTENTS OF THE PRESENT INVENTION

The present invention relates to a method for sequencing a polynucleotide, wherein sequential incorporation of different nucleotides is detected by the same luminescence signal, thereby realizing the sequencing of the polynucleotide.

In one aspect, the present invention relates to a method for determining a sequence of a target polynucleotide, which comprises:
(a) providing a target polynucleotide,
(b) contacting the target polynucleotide with a primer so that the primer hybridizes to the target polynucleotide, thereby forming a partial duplex of the target polynucleotide and the primer,
(c) contacting the partial duplex with a polymerase and a nucleotide under a condition that allows the polymerase to carry out a nucleotide polymerization reaction, so that the nucleotide is incorporated into the primer,
wherein the nucleotide is selected from one or more of the followings: a first nucleotide, a second nucleotide, a third nucleotide, and a fourth nucleotide, wherein the first nucleotide comprises a first nucleotide labeled with a first label and optionally an unlabeled first nucleotide, the second nucleotide comprises a second nucleotide labeled with a second label and optionally an unlabeled second nucleotide, the third nucleotide is selected from: (1) a third nucleotide labeled with the first label and a third nucleotide labeled with the second label, or (2) a third nucleotide simultaneously labeled with the first label and the second label, and the fourth nucleotide comprises an unlabeled fourth nucleotide,
wherein each nucleotide has a ribose or deoxyribose moiety that contains a protecting group attached thereto via a 2' or 3' oxygen atom,
(d) detecting the presence of the first label on the partial duplex of the step (c),
(e) detecting the presence of the second label on the partial duplex of the step (c),
(f) optionally removing the protecting group and the label on the nucleotide incorporated in the partial duplex of the step (c),
(g) optionally repeating the steps (c) to (f) one or more times to obtain sequence information of the target polynucleotide,
wherein the presence of the first label and the second label is detected by the same luminescence signal.

In a specific embodiment, the first label is a luminescent label.

In a specific embodiment, the step (d) comprises contacting the partial duplex of the step (c) with a ligand that is labeled with a luminescent label and specifically binds to the first label, and then detecting the presence of the luminescent label on the partial duplex.

In a specific embodiment, the ligand is removed when removing the protecting group and the label on the nucleotide incorporated in the partial duplex of the step (c).

In a specific embodiment, the step (e) comprises contacting the partial duplex of the step (c) with a ligand that is labeled with a luminescent label and specifically binds to the second label, and then detecting the presence of the luminescent label on the partial duplex.

In a specific embodiment, the step (e) is performed after the step (d).

In a specific embodiment, the luminescent labels are the same luminescent label.

In a specific embodiment, the luminescent label is a fluorescent label, such as a fluorophore, for example, selected from coumarin, AlexaFluor, Bodipy, fluorescein, tetramethylrhodamine, Cy5, Cy3, Texas red and derivatives thereof.

In a specific embodiment, in the first nucleotide, the first nucleotide labeled with the first label and the unlabeled first nucleotide have a ratio of 4:1 to 3:2.

In a specific embodiment, in the second nucleotide, the second nucleotide labeled with the second label and the unlabeled second nucleotide have a ratio of 4:1 to 3:2.

In another aspect, the present invention also relates to a kit for sequencing a polynucleotide, which comprises: (a) one or more nucleotides selected from the following: a first nucleotide, a second nucleotide, a third nucleotide and a fourth nucleotide, wherein the first nucleotide comprises a first nucleotide labeled with a first label and optionally an unlabeled first nucleotide, the second nucleotide comprises a second nucleotide labeled with a second label and optionally an unlabeled second nucleotide, the third nucleotide is selected from: (1) a third nucleotide labeled with the first label and a third nucleotide labeled with the second label, or (2) a third nucleotide simultaneously labeled with the first label and the second label, and the fourth nucleotide comprises an unlabeled fourth nucleotide; and (b) a packaging material for them, wherein the nucleotide each comprises a ribose or deoxyribose moiety that contains a protecting group attached via a 2' or 3' oxygen atom.

In a specific embodiment, the first label is a luminescent label.

In a specific embodiment, the kit further comprises a ligand that is labeled with a luminescent label and specifically binds to the first label.

In a specific embodiment, the kit further comprises a ligand that is labeled with a luminescent label and specifically binds to the second label.

In a specific embodiment, the luminescent labels are the same luminescent label.

In a specific embodiment, the luminescent label is a fluorescent label, such as a fluorophore, for example, selected from coumarin, AlexaFluor, Bodipy, fluorescein, tetramethylrhodamine, Cy5, Cy3, Texas red and derivatives thereof.

In a specific embodiment, the kit further comprises an enzyme and a buffer suitable for the enzyme to function.

SPECIFIC MODELS FOR CARRYING OUT THE PRESENT INVENTION

Figure 1:
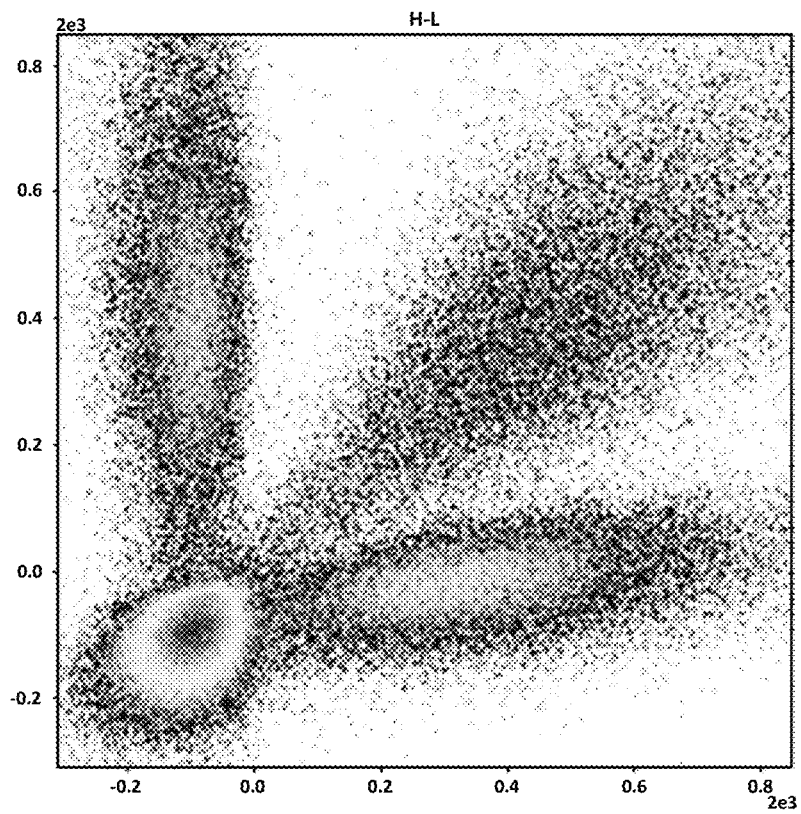
FIG. 1 shows a signal extraction diagram of the $1^{st}$ base during the sequencing of *E. coli* barcode sequence in Example 1.

Unless otherwise defined, all technical and scientific terms used herein have the same meaning as commonly understood by those of ordinary skill in the art to which the present invention belongs. All patents, applications and other publications mentioned herein are incorporated by reference in their entirety. If the definitions set forth herein conflict or are inconsistent with the definitions in patents, applications and other publications incorporated herein by reference, the definitions described herein shall prevail.

As used herein, the term "polynucleotide" refers to deoxyribonucleic acid (DNA), ribonucleic acid (RNA) or an analog thereof. A polynucleotide can be single-stranded, double-stranded, or contain both single-stranded and double-stranded sequences. A polynucleotide molecule can be derived from double-stranded DNA (dsDNA) form (e.g., genomic DNA, PCR and amplification products, etc.), or can be derived from single-stranded form of DNA (ssDNA) or RNA and it can be converted into dsDNA form, and vice versa. The exact sequence of the polynucleotide molecule can be known or unknown. The followings are illustrative examples of a polynucleotide: a gene or gene fragment (e.g., probe, primer, EST or SAGE tag), genomic DNA, genomic DNA fragment, exon, intron, messenger RNA (mRNA), transport RNA, ribosomal RNA, ribozyme, cDNA, recombinant polynucleotide, synthetic polynucleotide, branched polynucleotide, plasmid, vector, isolated DNA of any sequence, isolated RNA of any sequence, nucleic acid probe, primer or amplified copy of any of the above sequences.

The polynucleotide may comprise a nucleotide or nucleotide analog. A nucleotide usually contains a saccharide (e.g., ribose or deoxyribose), a base, and at least one phosphate group. Nucleotide may be abasic (i.e. lack of base). The nucleotide comprises a deoxyribonucleotide, modified deoxyribonucleotide, ribonucleotide, modified ribonucleotide, peptide nucleotide, modified peptide nucleotide, modified phosphate saccharide backbone nucleoside, and mixtures thereof. Examples of the nucleotide include, for example, adenosine monophosphate (AMP), adenosine diphosphate (ADP), adenosine triphosphate (ATP), thymidine monophosphate (TMP), thymidine diphosphate (TDP), thymidine triphosphate (TTP), cytidine monophosphate (CMP), cytidine diphosphate (CDP), cytidine triphosphate (CTP), guanosine monophosphate (GMP), guanosine diphosphate (GDP), guanosine triphosphate (GTP), uridine monophosphate (UMP), uridine diphosphate (UDP), uridine triphosphate (UTP), deoxyadenosine monophosphate (dAMP), deoxyadenosine diphosphate (dADP), deoxyadenosine triphosphate (dATP), deoxythymidine monophosphate (dTMP), deoxythymidine diphosphate (dTDP), deoxythymidine triphosphate (dTTP), deoxycytidine diphosphate (dCDP), deoxycytidine triphosphate (dCTP), deoxyguanosine monophosphate (dGMP), deoxyguanosine diphosphate (dGDP), deoxyguanosine triphosphate (dGTP), deoxyuridine monophosphate (dUMP), deoxyuridine diphosphate (dUDP) and deoxyuridine triphosphate (dUTP). Nucleotide analog containing a modified base may also be used in the method described herein. Whether it has a natural backbone or a similar structure, exemplary modified base that can be comprised in a polynucleotide includes, for example, inosine, xathanine, hypoxathanine, isocytosine, isoguanine, 2-aminopurine, 5-methyl cytosine, 5-hydroxymethylcytosine, 2-aminoadenine, 6-methyladenine, 6-methylguanine, 2-propylguanine, 2-propyladenine, 2-thiouracil, 2-thiothymine, 2-thiocytosine, 15-halogenated uracil, 15-halogenated cytosine, 5-propynyluracil, 5-propynylcytosine, 6-azouracil, 6-azocytosine, 6-azothymine, 5-uracil, 4-thiouracil, 8-halogenated adenine or guanine, 8-amino(adenine or guanine), 8-thio(adenine or guanine), 8-sulfanyl(adenine or guanine), 8-hydroxy(adenine or guanine), 5-halogenated uracil or cytosine, 7-methylguanine, 7-methyladenine, 8-azaguanine, 8-azaadenine, 7-deazaguanine, 7-deazaadenine, 3-deazaguanine, 3-deazaadenine, etc. As known in the art, certain nucleotide analogs, for example, nucleotide analogs such as adenosine 5'-phosphoryl sulfate, cannot be introduced into the polynucleotide.

Generally speaking, the nucleotide includes nucleotide A, C, G, T or U. As used herein, the term "nucleotide A" refers to a nucleotide containing adenine (A) or a modification or analog thereof, such as ATP, dATP. "Nucleotide G" refers to a nucleotide containing guanine (G) or a modification or analog thereof, such as GTP, dGTP. "Nucleotide C" refers to a nucleotide containing cytosine (C) or a modification or analog thereof, such as CTP, dCTP. "Nucleotide T" refers to a nucleotide containing thymine (T) or a modification or analog thereof, such as TTP, dTTP. "Nucleotide U" refers to a nucleotide containing uracil (U) or a modification or analog thereof, such as UTP, dUTP.

Labeling of Nucleotide

The present invention relates to labeling nucleotides with different labels, individually or in combination, so that different nucleotides can be distinguished, wherein the different labels can be detected by the same luminescent signal.

In a specific embodiment, the detection of different labels by the same luminescence signal is achieved by specifically binding the different labels to respective ligands labeled with luminescence labels that can generate the same luminescence signal. In a preferred embodiment, the luminescent labels that can generate the same luminescent signal are the same luminescent label.

As used herein, the label used to label the nucleotide and the ligand that specifically binds the label may be any molecules that can specifically bind to each other, and the binding pair is referred to herein as an anti-ligand pair. The binding between the members of the anti-ligand pair can be non-covalent. Anti-ligand pair needs not be limited to a pair of single molecules. For example, a single ligand can be bound by the synergistic effect of two or more anti-ligands. The binding between the members of the anti-ligand pair leads to the formation of a binding complex, sometimes called a ligand/anti-ligand complex or simply as a ligand/anti-ligand. Exemplary anti-ligand pairs include, but are not limited to: (a) hapten or antigenic compound combined with a corresponding antibody or binding part or fragment thereof, for example, digoxin-digoxin antibody, N3G-N3G antibody, FITC-FITC antibody; (b) nucleic acid aptamer and protein; (c) non-immune binding pair (e.g., biotin-avidin, biotin-streptavidin, biotin-neutravidin); (d) hormone-hormone binding protein; (e) receptor-receptor agonist or antagonist; (f) lectin-carbohydrate; (g) enzyme-enzyme cofactor; (h) enzyme-enzyme inhibitor; and (i) complementary oligonucleotide or polynucleotide pair capable of forming a nucleic acid duplex.

In another specific embodiment, one of the different labels can be a luminescent label, so that it can be directly detected. The other labels are still detected by specific binding to their respective ligands labeled with luminescent labels that can produce the same luminescent signal. In a preferred embodiment, the luminescent labels related to the different labels are the same luminescent label.

As used herein, the term "luminescent label" refers to any substance capable of emitting fluorescence at a specific emission wavelength when excited by a suitable excitation wavelength. Such a luminescent label may be, for example, a fluorophore, for example selected from coumarin, AlexaFluor, Bodipy, fluorescein, tetramethylrhodamine, phenoxazine, acridine, Cy5, Cy3, AF532, Texas red and derivatives thereof.

Sequencing of Polynucleotide

The nucleotides labeled with different labels alone or in combination of the present invention can be used in various nucleic acid sequencing methods. Preferably, the nucleotides labeled with different labels alone or in combination of the present invention are suitable for sequencing by synthesis. Sequencing by synthesis as used herein is a variety of sequencing by synthesis methods well known in the art. Basically, sequencing by synthesis involves first hybridizing a nucleic acid molecule to be sequenced with a sequencing primer, and then in the presence of a polymerase, polymerizing the labeled nucleotide as described herein at the 3' end of the sequencing primer by using the nucleic acid molecule to be sequenced as a template. After polymerization, the labeled nucleotide is identified by detecting the label. After the label (i.e., the chemiluminescent label as described herein) is removed from the labeled nucleotide, the next polymerization sequencing cycle starts.

In addition, the nucleic acid sequencing methods can also use the nucleotides described herein to perform the methods disclosed in U.S. Pat. No. 5,302,509.

The method for determining the sequence of a target polynucleotide can be carried out as follows: denaturing the target polynucleotide sequence, contacting the target polynucleotide with different nucleotides respectively, so as to form a complement of the target nucleotide, and detecting the incorporation of the nucleotides. The method utilizes polymerization, which allows the polymerase to extend the complementary strand by incorporating the correct nucleotides complementary to the target. The polymerization reaction also requires a special primer to initiate polymerization.

For each round of reaction, the incorporation of the labeled nucleotide is carried out through a polymerase, and the incorporation event is then measured. There are many different polymerases, and it is easy for a person of ordinary skill in the art to determine the most suitable polymerase. Preferred enzymes include DNA polymerase I, Klenow fragment, DNA polymerase III, T4 or T7 DNA polymerase, Taq polymerase or vent polymerase. It is also possible to use polymerases engineered to have specific properties.

The sequencing method is preferably performed on a target polynucleotide arranged on a solid support. A plurality of target polynucleotides can be immobilized on the solid support through a linker molecule, or can be attached to particles such as microspheres, and the particles can also be attached to a solid support material.

The polynucleotide can be attached to the solid support by a variety of methods, including the use of biotin-streptavidin interaction. Methods for immobilizing polynucleotides on a solid support are well known in the art and include lithography techniques and spotting each polynucleotide on a specific position on the solid support. Suitable solid supports are well known in the art and include glass slides and beads, ceramic and silicon surfaces, and plastic materials. The support is usually flat, although microbeads (microspheres) can also be used, and the latter can also be attached to other solid supports by known methods. The microspheres can have any suitable size, and their diameter is usually 10 to 100 nanometers. In a preferred embodiment, the polynucleotide is directly connected on a flat surface, preferably on a flat glass surface. The connection is preferably carried out in the form of covalent bond. The array used is preferably a single-molecule array, which includes polynucleotides located in a unique optically resolvable region, for example as described in the International Application No. WO00/06770.

The necessary conditions for polymerization are well known to those skilled in the art. In order to perform the polymerase reaction, usually a primer sequence must first be annealed to the target polynucleotide, in which the primer sequence is recognized by the polymerase and serves as the starting site for the subsequent extension of complementary strand. The primer sequence may be added as an independent component relative to the target polynucleotide. In addition, the primer and the target polynucleotide may be part of a single-stranded molecule, respectively, and an intramolecular duplex, that is, a hairpin loop structure, is formed by the primer part and a part of the target. The structure can be immobilized on the solid support at any position of the molecule. Other conditions necessary for carrying out the polymerase reaction are well known to those skilled in the art, and these conditions comprise temperature, pH, and buffer composition.

Subsequently, the labeled nucleotide of the present invention is brought into contact with the target polynucleotide to enable polymerization. The nucleotides can be added sequentially, that is, each kind of nucleotide (A, C, G or T/U) is added separately, or added at the same time.

The polymerization step is allowed to proceed for a time period sufficient to incorporate one nucleotide.

Unincorporated nucleotides are then removed, for example, by performing a washing step on the array, and detection of the incorporated label can then be performed.

The detection can be carried out by conventional methods. For example, methods of detecting fluorescent labels or signals are well known in the art. For example, it can be realized by a device that detects the wavelength of fluorescence. Such devices are well known in the art. For example, such a device may be a confocal scanning microscope that scans the surface of a solid support with a laser in order to image the fluorophore directly bound to the sequenced nucleic acid molecule. In addition, a sensitive 2-D detector such as a charge-coupled detector (CCD) can be used to observe each of the signals generated, for example. Other techniques such as Scanning Near Field Optical Microscopy (SNOM) can also be used, for example.

After detection, the label can be removed under suitable conditions.

The use of the labeled nucleotides of the present invention is not limited to DNA sequencing technology, and the nucleotides of the present invention can also be used to perform other forms including polynucleotide synthesis, DNA hybridization analysis, and single nucleotide polymorphism research. Any technique involving the interaction between nucleotides and enzymes can utilize the molecules of the present invention. For example, the molecule can be used as a substrate for reverse transcriptase or terminal transferase.

In a specific embodiment, the labeled nucleotide of the present invention also has a 3' protecting group. In some embodiments of the present invention, the protecting group and the label are usually two different groups on the 3'-blocked labeled nucleotide, but in other embodiments, the protecting group and the label can also be the same group.

As used herein, the term "protecting group" means a group that prevents the polymerase (which incorporates the nucleotide containing the group into the polynucleotide chain being synthesized) from continuously catalyzing the incorporation of another nucleotide after the nucleotide containing the group is incorporated into the polynucleotide chain being synthesized. Such protecting group is also referred to herein as 3'-OH protecting group. Nucleotides containing such protecting group are also referred to herein as 3' blocked nucleotides. The protecting group can be any suitable group that can be added to the nucleotide, as long as the protecting group can prevent additional nucleotide molecule from being added to the polynucleotide chain and can be removed from the saccharide portion of the nucleotide without damaging the polynucleotide chain. In addition, the nucleotide modified by protecting group should be capable of being resistant to polymerase or other suitable enzymes for incorporating the modified nucleotides into the polynucleotide chain. Therefore, the ideal protecting group exhibits long-term stability, can be efficiently incorporated by polymerase, prevents secondary or further incorporation of nucleotides, and can be removed under mild conditions that do not damage the structure of the polynucleotide, preferably under aqueous conditions.

The prior art has described a variety of protecting groups that meet the above description. For example, WO 91/06678 discloses 3'-OH protecting groups, including esters and ethers, —F, —$NH_2$, —$OCH_3$, —$N_3$, —$OPO_3$, —$NHCOCH_3$, 2-nitrophenyl carbonate, 2,4-sulfenyldinitro and tetrahydrofuran ether. Metzker et al. (Nucleic Acids Research, 22(20): 4259-4267, 1994) disclose the synthesis of eight 3'-modified 2-deoxyribonucleoside 5'-triphosphates (3'-modified dNTPs) and applications thereof. WO2002/029003 describes the use of an allyl protecting group to cap a 3'-OH group of the growing DNA strand in polymerase reaction. Preferably, various protecting groups reported in the International Application Publications WO2014139596 and WO2004/018497 can be used, which include, for example, those protecting groups illustrated in FIG. 1A of WO2014139596 and those 3' hydroxyl protecting groups (i.e., protecting groups) defined in the claims, and those protecting groups exemplified in FIG. 3 and FIG. 4 of WO2004/018497 as well as those protecting groups defined in the claims. The above references are all incorporated herein by reference in their entirety.

Those skilled in the art will understand how to attach a suitable protecting group to the ribose ring so as to block the interaction with 3'-OH. The protecting group can be directly attached to the 3' position or can be attached to the 2' position (the protecting group has sufficient size or charge to block the interaction at the 3' position). In addition, the protecting group can be attached to the 3' and 2' positions, and can be cleaved to expose 3'-OH group.

After successfully incorporating the 3'-blocked nucleotide into the nucleic acid strand, the sequencing protocol requires the removal of the protecting group to produce a usable 3'-OH site for continuous strand synthesis. The reagents that can remove the protecting group from the modified nucleotide as used herein depend to a large extent on the protecting group used. For example, the removal of ester protecting group from the 3'-hydroxyl functional group is usually accomplished by alkaline hydrolysis. The ease of removing the protecting group varies greatly; generally, the greater the electronegativity of the substituent on the carbonyl carbon, the greater the ease of removal. For example, the highly electronegative trifluoroacetic acid group can be rapidly cleaved from the 3'-hydroxyl at pH 7 in methanol (Cramer et al., 1963), so it is unstable during polymerization at this pH. Phenoxyacetate group can be cleaved within less than 1 minute, but a significantly higher pH is required, for example, NH—/methanol is used for implementation (Reese and Steward, 1968). Various hydroxy protecting groups can be selectively cleaved using chemical methods other than alkaline hydrolysis. The 2,4-dinitrophenylthio group can be quickly cleaved by treatment with nucleophiles such as thiophenol and thiosulfate (Letsinger et al., 1964). Allyl ether is cleaved by treatment with Hg(II) in acetone/water (Gigg and Warren, 1968). Tetrahydrothiopyranyl ether is cleaved by using Ag(I) or Hg(II) under neutral conditions (Cohen and Steele, 1966; Cruse et al., 1978). Photochemical deblocking can be used together with photochemically cleavable protecting groups. Several protecting groups can be used in this method. The use of o-nitrobenzyl ether as protecting group for 2'-hydroxyl of ribonucleoside is known and confirmed (Ohtsuka et al., 1978); it is removed by irradiation at 260 nm. Alkylcarbonyl o-nitrobenzyl carbonate is also removed by irradiation at pH 7 (Cama and Christensen, 1978). Enzymatic deblocking of 3'-OH protecting group is also possible. It has been demonstrated that T4 polynucleotide kinase can convert 3'-phosphate terminus into 3'-hydroxyl terminus, which can then be used as a primer for DNA polymerase I (Henner et al., 1983). This 3'-phosphatase activity is used to remove the 3' protecting group of those dNTP analogs containing phosphate as protecting group.

Other reagents that can remove protecting groups from 3'-blocked nucleotides include, for example, phosphine (e.g., tris(hydroxymethyl)phosphine (THP)), which can, for example, remove azide-containing 3'-OH protecting group from nucleotide (for this application of phosphine, see, for example, the description in WO2014139596, which is incorporated herein by reference in its entirety). Other reagents that can remove protecting groups from 3'-blocked nucleotides also include, for example, the corresponding reagents described on pages 114-116 of the specification of WO2004/018497 that remove 3'-allyl, 3,4-dimethoxybenzyloxymethyl or fluoromethoxymethyl as 3'-OH protecting groups.

In the embodiment of the present invention, the label of nucleotide is preferably removed together with the protecting group after detection.

In certain embodiments, the label may be incorporated into the protecting group, thereby allowing the label to be removed along with the protecting group after the 3'-blocked nucleotide has been incorporated into the nucleic acid strand.

In other embodiments, by using a linking group, the label and the protecting group can be attached to the nucleotide separately. Such a label may, for example, be attached to the purine or pyrimidine base of the nucleotide. In certain embodiments, the linking group used is cleavable. The use of a cleavable linking group ensures that the label can be removed after detection, which avoids any signal interference with any labeled nucleotides subsequently incorporated. In other embodiments, a non-cleavable linking group may be used, because after the labeled nucleotide is incorporated into the nucleic acid strand, subsequent nucleotide incorporation is not required, so there is no need to remove the label from the nucleotide.

In other embodiments, the label and/or linking group may have a size or structure sufficient to block the incorporation of other nucleotides into the polynucleotide chain (that is, the label itself can serve as a protecting group). The blocking may be due to steric hindrance, or may be due to a combination of size, charge and structure.

The cleavable linking group is well known in the art, and conventional chemical methods can be used to connect the linking group to the nucleotide base and the label. The linking group can be attached to any position of the nucleotide base, provided that Watson-Crick base pairing can still be performed. For purine base, it would be preferred if the linking group is connected through position 7 of the purine or preferably deaza purine analog, through 8-modified purine, through N-6 modified adenine or N-2 modified guanine. For pyrimidine, it is preferred that the connection is fulfilled through position 5 on cytosine, thymine and uracil, and position N-4 on cytidine.

The use of the term "cleavable linking group" does not mean that the entire linking group needs to be removed (e.g., removed from the nucleotide base). When the label is connected to the base, the nucleoside cleavage site can be located at a position on the linking group, which can ensure that a part of the linking group remains connected to the nucleotide base after cleavage.

Suitable linking groups include, but are not limited to, disulfide linking group, acid-labile linking group (including dialkoxybenzyl linking group, Sieber linking group, indole linking group, tert-butyl Sieber linking group), electrophilic cleavable linking group, nucleophilic cleavable linking group, photo-cleavable linking group, linking group that can be cleaved under reducing conditions and oxidizing conditions, safety-catch linking group, and linking group that can be cleaved through elimination mechanisms. Suitable linking groups can be modified with standard chemical protecting groups, as disclosed in the following documents: Greene & Wuts, Protective Groups in Organic Synthesis, John Wiley & Sons. Guillier et al. disclose other suitable cleavable linking groups for solid phase synthesis (Chem. Rev. 100:2092-2157, 2000).

The linking group can be cleaved by any suitable method, including exposure to acid, base, nucleophile, electrophile, free radical, metal, reducing or oxidizing reagent, light, temperature, enzyme, etc., and suitable way of cleavage for each cleavable linking group will be exemplarily described below. Generally, the cleavable linking group can be cleaved under the same conditions as the protecting group, so that only one treatment is required to remove the label and protecting group.

Electrophilic cleavable linking groups are typically cleaved by protons, and include acid-sensitive cleavable ones. Suitable electrophilic cleavable linking groups include modified benzyl systems such as trityl, p-oxybenzyl ester, and p-hydrocarbonyloxybenzyl amide. Other suitable linking groups include tert-butoxycarbonyl (Boc) group and acetal systems. To prepare suitable linking molecules, it is also possible to consider the use of thiophilic metals such as nickel, silver or mercury in the cleavage of thioacetals or other sulfur-containing protecting groups. Nucleophilic cleavable linking groups include groups that are unstable in water (i.e., can be simply cleaved at alkaline pH), such as esters, and groups that are unstable to non-aqueous nucleophiles. Fluoride ions can be used to cleave silicon-oxygen bonds in groups such as triisopropylsilane (TIPS) or tert-butyldimethylsilane (TBDMS). Photodegradable linking groups are widely used in saccharide chemistry. Preferably, the light required to activate cleavage does not affect other components in the modified nucleotide. For example, if a fluorophore is used as a label, it is preferable that the fluorophore absorbs light of a different wavelength than that required to cleave the linking molecule. Suitable linking groups include those based on O-nitrobenzyl compounds and nitroveratryl compounds. Linking groups based on benzoin chemistry can also be used (Lee et al., J. Org. Chem. 64:3454-3460, 1999). Various linking groups that are sensitive to reductive cleavage are known. Catalytic hydrogenation using palladium-based catalysts has been used to cleave benzyl and benzyloxycarbonyl groups. Disulfide bond reduction is also known in the art. Methods based on oxidation are well known in the art. These methods include the oxidation of hydrocarbonyloxybenzyl and the oxidation of sulfur and selenium linking groups. It is also within the scope of the present invention to use aqueous iodine to cleave disulfide and other sulfur- or selenium-based linking groups. Safety-catch linkers are those that are cleaved in two steps. In a preferred system, the first step is the generation of reactive nucleophilic center, and the subsequent second step involves intramolecular cyclization, which results in cleavage. For example, levulinate linkage can be treated with hydrazine or photochemical methods to release an active amine, and the amine is then cyclized to cleave the ester elsewhere in the molecule (Burgess et al., J. Org. Chem. 62: 5165-5168, 1997). Elimination reactions can also be used to cleave the linking group. Base-catalyzed elimination of groups such as fluorenylmethyloxycarbonyl and cyanoethyl and palladium-catalyzed reduction elimination of allyl systems can be used.

In certain embodiments, the linking group may include a spacer unit. The length of the linking group is not important, as long as the label and the nucleotide are kept at a sufficient distance so as not to interfere with the interaction between the nucleotide and the enzyme.

In certain embodiments, the linking group may consist of a functional group similar to the 3'-OH protecting group.

This will allow only a single treatment to remove the label and protecting group. A particularly preferred linking group is an azide-containing linking group cleavable by phosphine.

The reagents that can remove the label from the modified nucleotide as used herein depend to a large extent on the label used. For example, in the case where a protecting group is incorporated into the label, the protecting group-removing reagent described above is used to remove the label. Alternatively, when the label is linked to the base of the nucleotide through a cleavable linking group, the label is removed using a reagent that cleaves the linking group as described above. In a preferred embodiment, the same reagent is used to remove the label and protecting group from the modified nucleotide, for example where the linking group consists of a functional group similar to the 3'-OH protecting group.

Exemplary Embodiments of the Present Invention

In a specific embodiment, the present invention relates to a method for determining a sequence of a target polynucleotide, which comprises:
(a) providing a target polynucleotide,
(b) contacting the target polynucleotide with a primer so that the primer hybridizes to the target polynucleotide, thereby forming a partial duplex of the target polynucleotide and the primer,
(c) contacting the partial duplex with a polymerase and a nucleotide under a condition that allows the polymerase to carry out a nucleotide polymerization reaction, so that the nucleotide is incorporated into the primer,
wherein the nucleotide is selected from one or more of the following: a first nucleotide, a second nucleotide, a third nucleotide, and a fourth nucleotide, wherein the first nucleotide comprises a first nucleotide labeled with a first label, the second nucleotide comprises a second nucleotide labeled with a second label, the third nucleotide is selected from: (1) a third nucleotide labeled with the first label and a third nucleotide labeled with the second label, or (2) a third nucleotide simultaneously labeled with the first label and the second label, and the fourth nucleotide comprises an unlabeled fourth nucleotide,
wherein each nucleotide has a ribose or deoxyribose moiety that contains a protecting group attached thereto via a 2' or 3' oxygen atom,
wherein the first label is a luminescent label,
(d) detecting the presence of the luminescent label on the partial duplex of the step (c),
(e) subsequently contacting the partial duplex of the step (c) with a ligand that is labeled with a luminescent label and specifically binds to the second label, and then detecting the presence of the luminescent label on the partial duplex,
(f) optionally removing the protecting group and label on the nucleotide incorporated in the partial duplex of the step (c),
(g) optionally repeating the steps (c) to (f) one or more times to obtain sequence information of the target polynucleotide,
wherein the luminescent labels are the same luminescent label.

In another specific embodiment, the present invention relates to a method for determining a sequence of a target polynucleotide, which comprises:

(a) providing a target polynucleotide,
(b) contacting the target polynucleotide with a primer so that the primer hybridizes to the target polynucleotide, thereby forming a partial duplex of the target polynucleotide and the primer,
(c) contacting the partial duplex with a polymerase and a nucleotide under a condition that allows the polymerase to carry out a nucleotide polymerization reaction, so that the nucleotide is incorporated into the primer,
wherein the nucleotide is selected from one or more of the following: a first nucleotide, a second nucleotide, a third nucleotide, and a fourth nucleotide, wherein the first nucleotide comprises a first nucleotide labeled with a first label, the second nucleotide comprises a second nucleotide labeled with a second label, the third nucleotide is selected from: (1) a third nucleotide labeled with the first label and a third nucleotide labeled with the second label, or (2) a third nucleotide simultaneously labeled with the first label and the second label, and the fourth nucleotide comprises an unlabeled fourth nucleotide,
wherein each nucleotide has a ribose or deoxyribose moiety that contains a protecting group attached thereto via a 2' or 3' oxygen atom,
(d) contacting the partial duplex of the step (c) with a ligand that is labeled with a luminescent label and specifically binds to the first label, and then detecting the presence of the luminescent label on the partial duplex,
then removing the ligand from the partial duplex,
(e) contacting the partial duplex of the step (c) with a ligand that is labeled with a luminescent label and specifically binds to the second label, and then detecting the presence of the luminescent label on the partial duplex,
(f) optionally removing the protecting group and label on the nucleotide incorporated in the partial duplex of the step (c),
(g) optionally repeating the steps (c) to (f) one or more times to obtain sequence information of the target polynucleotide,
wherein the luminescent labels are the same luminescent label.

Improved Embodiments of the Present Invention

In the process of developing the present invention, the inventors also found that by adding a part of unlabeled nucleotides, the signal value generated by a single labeled nucleotide can be controlled, which is beneficial to the differentiation of different nucleotides and subsequent data analysis and significantly improves sequencing results.

Therefore, in a specific embodiment, in addition to the first nucleotide labeled with the first label, the first nucleotide may also comprise an unlabeled first nucleotide. In addition to the second nucleotide labeled with the second label, the second nucleotide may also comprise an unlabeled second nucleotide.

In a specific embodiment, as for the first nucleotide, the first nucleotide labeled with the first label and the unlabeled first nucleotide have a ratio of 4:1 to 3:2. In a specific embodiment, as for the second nucleotide, the second nucleotide labeled with the second label and the unlabeled second nucleotide have a ratio of 4:1 to 3:2.

The Beneficial Technical Effect of the Present Invention

In the present invention, the sequencing is performed only based on a single excitation fluorescence detection. Compared with the detection method using 4 or 2 kinds of fluorescent dyes to label 4 kinds of nucleotides, the sequencing method only requires a single excitation light source and a single camera, which can reduce the size of and the manufacturing cost of the sequencing equipment.

The present invention generates only one kind of fluorescence during the sequencing process, and can avoid interference between different fluorescent signals caused by labeling different fluorescent dyes. Compared with the detection of labeling 2 kinds of fluorescent dyes, it also avoids the mutual interference of dual-color fluorescence and single-color fluorescence.

Compared with the Roche sequencing method and the Ion torrent sequencing method, the 3'-terminal hydroxyl of the nucleotide used in the present invention is modified and blocked, so that during the sequencing process, only one deoxyribonucleotide can be synthesized per reaction, and it will not occur that a plurality of deoxyribonucleotides are synthesized in one reaction when a sequence with repeated bases is encountered in the sequencing process using natural deoxyribonucleotides. Therefore, the present invention is helpful to improve the accuracy of sequencing.

EXAMPLE

Example 1

Brief Description of Method
(1) A nucleic acid molecule to be sequenced that was connected to a support was provided, or a nucleic acid molecule to be sequenced was connected to a support;
(2) A primer for initiating a nucleotide polymerization reaction was added, the primer was annealed to the nucleic acid molecule to be sequenced, and the primer served as an initial growing nucleic acid strand and formed together with the nucleic acid molecule to be sequenced a duplex connected to the support;
(3) A polymerase for the nucleotide polymerization and four kinds of nucleotides were added to form a reaction system containing a solution phase and a solid phase; wherein, the four kinds of nucleotides were derivatives of nucleotides A, (T/U), C and G, and had the ability of base complementary pairing; hydroxyl (—OH) at the 3' position of ribose or deoxyribose of the four compounds was protected by a protecting group; and, a first nucleotide (e.g., nucleotide A) was connected to a first molecular label (e.g., biotin, N3G and other small molecules), a second nucleotide (e.g., nucleotide T) was connected to a second molecular label (e.g., digoxin, FITC, etc.), a third nucleotide (e.g., nucleotide C) was partially connected with the first molecular label and the second molecular label, and a fourth nucleotide (e.g., nucleotide G) was not connected with a molecular label. In order to facilitate the differentiation between different nucleotides and subsequent data analysis, the signal value generated by a single labeled nucleotide was controlled, and some corresponding unlabeled nucleotides such as A-cold and T-cold were added. The labeled nucleotide A and the A-cold had a ratio ranging from 4:1 to 3:2; the labeled nucleotide T and the T-cold had a ratio ranging from 4:1 to 3:2. The four kinds of nucleotides had a final concentration between 0.5 µM and 5 µM in the reaction solution.
(4) Under the condition that the polymerase was allowed to carry out the nucleotide polymerization reaction, 150 to 200 µl of polymerization reaction solution was added at a rate of 150 to 350 µl/min, the reaction temperature was 40° C. to 60° C., and the reaction time was 1 to 2 minutes, so that one of the four nucleotides was incorporated into the 3'-terminus of the growing nucleic acid strand;
(5) 300 to 400 µl of elution reagent (PBS or TBS) was used at a rate of 150 to 350 µl/min to remove the solution phase of the reaction system in the previous step, and the duplex connected to the support was retained. 150 to 200 µl of a ligand (e.g., SA, N3G antibody, etc.) that specifically bound to the first molecular label (biotin, N3G, etc.) was added at a rate of 150 to 350 µl/min, the ligand was labeled with a fluorescent group (e.g., AF532, CY3, etc.), and incubation was carried out for 1 to 5 minutes at 30° C. to 55° C. Then, 300 to 400 µl of elution reagent (PBS or TBS) was used at a rate of 150 to 350 µl/min to elute the free fluorescent label-labeled ligand, and the emitted fluorescence signal was detected in a photographing buffer under 50 to 1000 ms exposure conditions.
(6) 300 to 400 µl of elution reagent (PBS or TBS) was used at a rate of 150 to 350 µl/min to replace the aforementioned photographing buffer, and then 150 to 200 µl of a ligand (digoxin antibody, FITC antibody, etc.) specifically bound to the second molecular label (digoxin, FITC, etc.) was added at a rate of 150 to 350 µl/min, the ligand was labeled with a fluorophore (e.g., AF532, CY3, etc.), and incubation was carried out at 30° C. to 55° C. for 1 to 5 minutes. Then, 300 to 400 µl of elution reagent (PBS or TBS) was used at a rate of 150 to 350 µl/min to elute the free fluorescent label-labeled antibody, and the emitted fluorescent signal was detected in a photographing buffer under 10 to 200 ms exposure conditions.
(7) After the detection was completed, 300 to 400 µl of cleavage buffer was introduced with a rate of 150 to 200 ul/min, and incubation was carried out at 50° C. to 60° C. for 1 to 2 minutes, and the small molecule label attached to the deoxyribonucleotide analog and the hydroxyl (—OH) protecting group at the 3' position were removed at the same time.
(8) The steps (3) to (7) were repeated.
(9) The collected signals were analyzed by software and converted into sequence information.

Determination and Analysis of E. coli Barcode Sequence

Nucleotides were labeled with biotin and digoxin, and streptavidin and digoxin-antibody were used as their corresponding ligands.

1. Experimental Materials
    1). E. coli
    2). BGISEQ-500 high-throughput sequencing kit (SE100) MGIEasy™ DNA Library Preparation Kit
    3). Deoxyribonucleotide analogs and polymerization reaction mixed solution
(1) Biotin-Modified Adenine Deoxyribonucleotide Analog

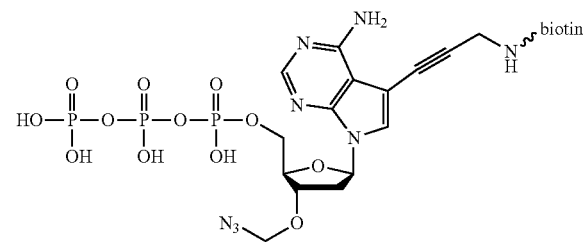

(2) Biotin-Modified Cytosine Deoxyribonucleotide Analog

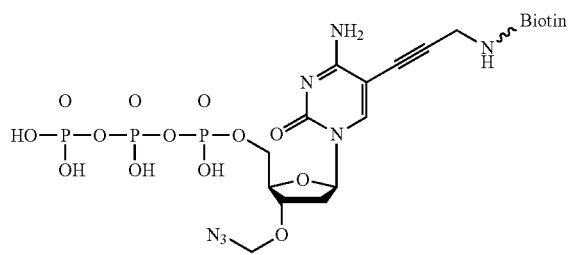

(3) Digoxin-Modified Cytosine Deoxyribonucleotide Analogue

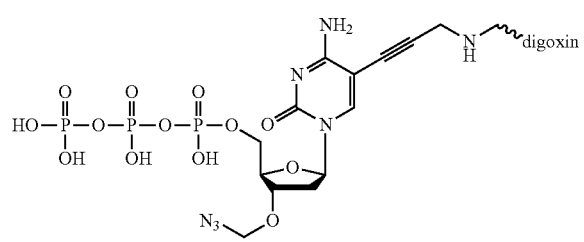

(4) Digoxin-Modified Thymine Deoxyribonucleotide Analogue

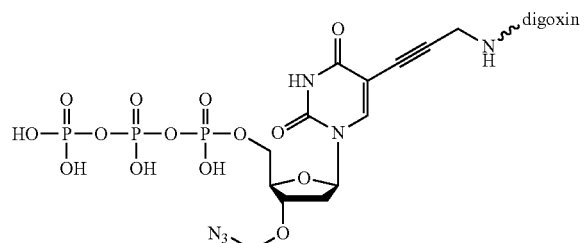

(5) Guanine Deoxyribonucleotide Analogue

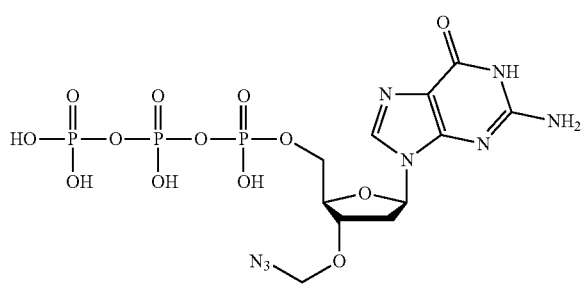

Mixed reaction solution 1 of deoxyribonucleotide analogues:

The first group: A-biotin+A-cold (A-biotin: A-cold was 4:1, A-biotin+A-cold=1 μM)

The second group: C-biotin+C-digoxin (C-biotin:C-digoxin was 2:1, C-biotin+C-digoxin=2 μM)

The third group: T-digoxin+T-cold (T-digoxin:T-cold was 4:1, T-digoxin+T-cold=1 μM)

The fourth group: G-cold (1 μM)

The four groups of nucleotide analogues were formulated into a mixed solution according to the above concentration and ratio.

Mixed reaction solution 2 of deoxyribonucleotide analogs:

The first group: A-biotin (1 μM)

The second group: C-biotin+C-digoxin (C-biotin:C-digoxin was 2:1, C-biotin+C-digoxin=2 μM)

The third group: T-digoxin (1 μM)

The fourth group: G-cold (1 μM)

The four groups of nucleotide analogues were formulated into a mixed solution according to the above concentration and ratio.

4). Phosphate buffered saline (PBS) (Shenggong Bio)

This reagent was used as both antibody ligand buffer and elution reagent.

5). 2 μg/ml CY3 fluorescence labeled with streptavidin (reagent manufacturer: Thermo Fisher scientific; reagent item number: 434315); 2 μg/ml CY3 fluorescence labeled with digoxin antibody (reagent manufacturer: Jackson ImmunoResearch; reagent item number: 200-162-156).

The above-mentioned fluorescently labeled antibodies were all formulated with PBS.

2. Experimental Steps

1) *E. coli* genomic DNA was extracted by referring to the following documents.

So A, Pel J, Rajan S, Marziali A. Efficient genomic DNA extraction for low target concentration bacterial cultures using SCODA DNA extraction technology. Cold Spring Harb Protoc. 2010 (10): pdb. prot5506.

2) Circular single-stranded DNA was prepared by referring to the MGIEasy™ DNA library preparation kit and instructions thereof. The prepared single-stranded circular DNA had been labeled with a barcode sequence.

3) By referring to the instructions of BGISEQ-500 High-throughput Sequencing Kit (SE100), the circular single-stranded DNA was copied through rolling circle to prepare DNA nanospheres. Then, by continuously referring to the instructions of BGISEQ-500 High-throughput Sequencing Kit (SE100), the prepared DNA nanospheres were loaded on sequencing chip.

4) Phosphate buffer solution (Shenggong) was introduced with a flow volume of 300 μl and a flow rate of 200 ul/min into the chip loaded with DNA nanospheres.

5) By referring to the instructions of BGISEQ-500 High-throughput Sequencing Kit (SE100), the sequencing reaction solution was prepared, and the deoxyribonucleotides therein were replaced with the 4 groups of deoxynucleotide analogues 1 or deoxynucleotide analogues 2 in the above experimental materials, the concentrations thereof referred to the experimental materials. The newly prepared sequencing reaction solution was introduced into the chip, with a flow volume of 300 μl and a flow rate of 200 ul/min. Incubation was carried out at 55° C. for 1 min. Then, the phosphate buffer (Shenggong) was introduced with a flow volume of 300 μl and a flow rate of 200 ul/min.

6) Streptavidin-labeled CY3 fluorescence (2 μg/ml, Thermo Fisher) was introduced into the sequencing chip with a flow volume of 150 μl and a flow rate of 150 ul/min, so that the fluorescent-labeled streptavidin and biotin are combined. Incubation was carried out at 35° C. for 3 min. Then, phosphate buffer (Shenggong) was introduced with a flow volume of 300 μl and a flow rate of 200 ul/min to remove free streptavidin-labeled CY3 fluorescence.

7) Signal acquisition buffer (available in the BGISEQ-500 High-throughput Sequencing Kit (SE100)) was introduced into the sequencing chip with a flow volume of 300 µl and a flow rate of 200 ul/min, and then the fluorescence bound on the sequence to be tested was excited by laser (exposure time was 100 ms) and the resultant signal was recorded.

8) Phosphate buffer (Shenggong) was introduced into the sequencing chip with a flow volume of 300 µl and a flow rate of 200 ul/min. Then, digoxin antibody-labeled CY3 fluorescence (2 µg/ml, Jackson ImmunoResearch) was introduced with a flow volume of 150 µl and a flow rate of 150 ul/min, and incubation was carried out at 35° C. for 5 min. Then, phosphate buffer (Shenggong) was introduced with a flow volume of 300 µl and a flow rate of 200 ul/min to remove the free digoxin antibody-labeled CY3 fluorescence.

9) Signal acquisition buffer was introduced into the sequencing chip with a flow volume of 300 µl and a flow rate of 200 ul/min. Then, the fluorescence bound to the sequence to be tested was excited by laser (exposure time was 20 ms) and the resultant signal was recorded.

10) Cleavage reaction solution (available in the BGISEQ-500 High-throughput Sequencing Kit (SE100)) was introduced with a flow volume of 300 µl and a flow rate of 200 ul/min, and incubation was carried out at 57° C. for 1 min.

11) The steps 4 to 10 were cyclically repeated.

12) The fluorescent signal information recorded in each reaction cycle was converted into deoxyribonucleotide information by analysis software.

13) A total of 10 sequencing reaction cycles (for sequencing of barcodes) were performed, and the resolution of barcodes was carried out for all read lengths according to the software of the 500 platform, and the resolution rate of each barcode was calculated.

3. Experimental Results

According to the analysis of barcode sequence analysis software, the barcode resolution efficiency was 82%.

FIG. 1 was a signal extraction diagram of the $1^{st}$ base of the barcode sequence to be tested. It could be seen from the diagram that 4 kinds of deoxyribonucleotides were divided into 4 signal groups according to the detection rules. The lower left corner was the G base signal group; the horizontal signal arm was the A base signal group; the vertical signal arm was the T base signal group; and the signal arm between the A and T signal arms was the C base signal group.

Figure 2:
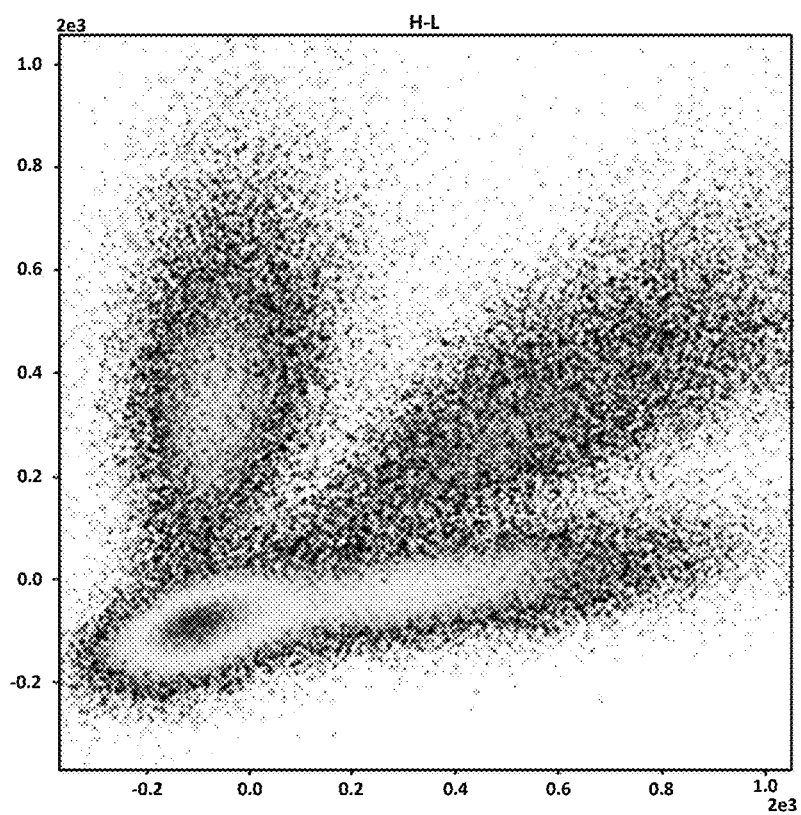
FIG. 2 shows a signal extraction diagram of the $10^{th}$ base during the sequencing of *E. coli* barcode sequence in Example 1.

FIG. 2 was a signal extraction diagram of the $10^{th}$ base of the barcode sequence to be tested, and the differentiation of signal arms was identical to that of the signal extraction diagram of the $1^{st}$ base.

Figure 5:
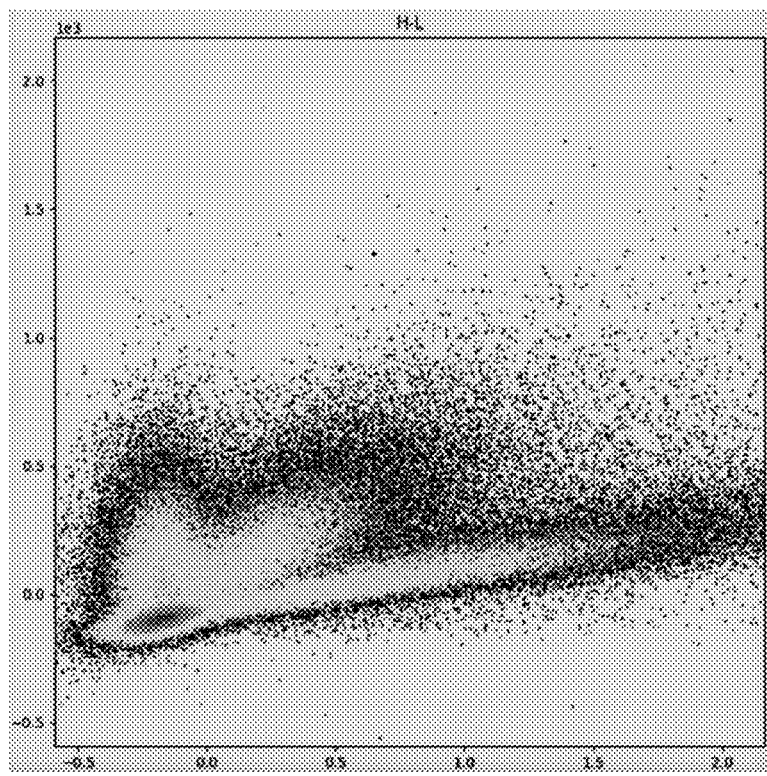
FIG. 5 shows a signal extraction diagram of the $1^{st}$ base during the experiment without adding an unlabeled nucleotide in Example 1.

FIG. 5 was a signal extraction diagram of the $1^{st}$ base in the experiment without adding an unlabeled nucleotide, and the differentiation of signal arms was identical to that of the aforementioned experiment with adding unlabeled nucleotides.

In addition, 50 sequencing reaction cycles were performed using the same experimental method described above, and the analysis showed that the mapping rate was 70% and the error rate was 2%.

Example 2

Brief Description of Method (1) A nucleic acid molecule to be sequenced that was connected to a support was provided, or a nucleic acid molecule to be sequenced was connected to a support;

(2) A primer for initiating a nucleotide polymerization reaction was added, the primer was annealed to the nucleic acid molecule to be sequenced, and the primer served as an initial growing nucleic acid strand and formed together with the nucleic acid molecule to be sequenced a duplex connected to the support;

(3) A polymerase for the nucleotide polymerization and four kinds of nucleotides were added to form a reaction system containing a solution phase and a solid phase; wherein, the four kinds of nucleotides were derivatives of nucleotides A, (T/U), C and G, and had the ability of base complementary pairing; hydroxyl (—OH) at the 3' position of ribose or deoxyribose of the four nucleotides was protected by a protecting group; and, a first nucleotide (e.g., nucleotide A) was connected to a first molecular label (any excitable fluorescence, such as AF532, CY3, etc.), a second nucleotide (e.g., nucleotide T) was connected to a second molecular label (e.g., biotin, digoxin and other small molecules), a third nucleotide (e.g., nucleotide C) was partially connected with the first molecular label and the second molecular label, and a fourth nucleotide (e.g., nucleotide G) was not connected with a molecular label. In order to facilitate the differentiation between different nucleotides and subsequent data analysis, the signal value generated by single labeled nucleotide was controlled, and some corresponding unlabeled nucleotides such as A-cold and T-cold were added. The labeled nucleotide A and the A-cold had a ratio ranging from 4:1 to 3:2; the labeled nucleotide T and the T-cold had a ratio ranging from 4:1 to 3:2. The four kinds of deoxyribonucleotide analogues had a final concentration between 0.5 µM and 5 µM in the reaction solution.

(4) Under the condition that the polymerase was allowed to carry out the nucleotide polymerization reaction, 150 to 200 µl of polymerization reaction solution was added at a rate of 150 to 350 µl/min, the reaction temperature was 40° C. to 60° C., and the reaction time was 1 to 2 minutes, so that one of the four nucleotides was incorporated into the 3'-terminus of the growing nucleic acid strand;

(5) 300 to 400 µl of elution reagent (PBS or TBS) was used at a rate of 150 to 350 µl/min to remove the solution phase of the reaction system in the previous step, and the duplex connected to the support was retained. The emitted fluorescence signal was detected in a photographing buffer under 50 to 1000 ms exposure conditions.

(6) 300 to 400 µl of elution reagent (PBS or TBS) was used at a rate of 150 to 350 µl/min to replace the aforementioned photographing buffer, and then 150 to 200 µl of a ligand (SA, digoxin antibody, etc.) specifically bound to the second molecular label (biotin, digoxin, etc.) was added at a rate of 150 to 350 µl/min, the ligand was labeled with a fluorescent group (the same fluorescence as the first molecule label), and incubation was carried out at 30° C. to 55° C. for 1 to 5 minutes. Then, 300 to 400 µl of elution reagent (PBS or TBS) was used at a rate of 150 to 350 µl/min to elute the free fluorescent-labeled antibody, and the emitted fluorescent signal was detected in a photographing buffer under 10 to 200 ms exposure conditions.

(7) After the detection was completed, 300 to 400 µl of cleavage buffer was introduced with a rate of 150 to 200 ul/min, and incubation was carried out at 50° C. to 60° C. for 1 to 2 minutes, and the small molecule label attached to the deoxyribonucleotide analog and the hydroxyl (—OH) protecting group at the 3' position were removed at the same time.

(8) The steps (3) to (7) were repeated.

(9) The collected signals were analyzed by software and converted into sequence information.

Determination and Analysis of *E. coli* SE50

1. Experimental Materials

1) *E. coli*

2) BGISEQ-500 high-throughput sequencing kit (SE100) MGIEasy™ DNA Library Preparation Kit 3) Deoxyribonucleotide analogs and polymerization reaction mixed solution (1) Fluorescent AF532-Modified Adenine Deoxyribonucleotide Analogue

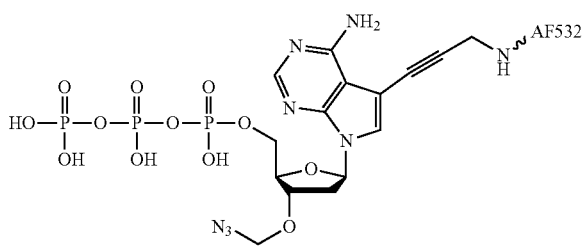

(2) Fluorescent AF532-Modified Cytosine Deoxyribonucleotide Analogue

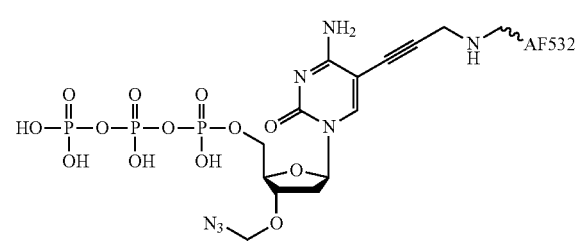

(3) Biotin-Modified Cytosine Deoxyribonucleotide Analogue

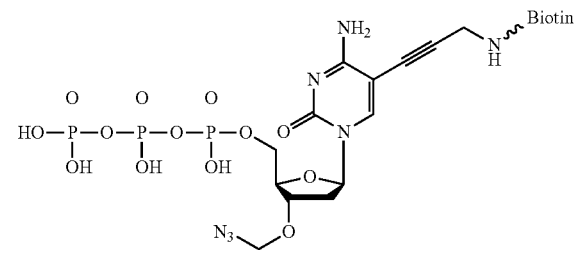

(4) Biotin-Modified Thymine Deoxyribonucleotide Analogue

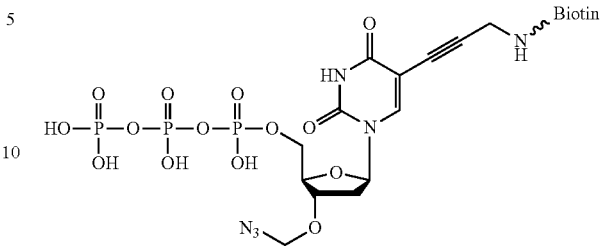

(5) Guanine Deoxyribonucleotide Analogue

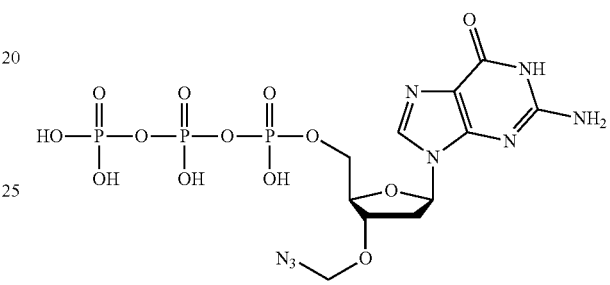

Mixed reaction solution 1 of deoxyribonucleotide analogues:

The first group: A-AF532+A-cold (A-biotin:A-cold was 4:1, A-biotin+A-cold=1 μM)

The second group: C-biotin+C-AF532 (C-biotin:C-AF532 was 2:1, C-biotin+C-AF532=2 μM)

The third group: T-biotin+T-cold (T-biotin:T-cold is 4:1, T-biotin+T-cold=1 μM)

The fourth group: G-cold (1 μM)

The four groups of nucleotide analogues were prepared into a mixed solution according to the above concentration and ratio.

Mixed reaction solution 2 of deoxyribonucleotide analogs:

The first group: A-AF532 (1 μM)

The second group: C-biotin+C-AF532 (C-biotin:C-AF532 was 2:1, C-biotin+C-AF532=2 μM)

The third group: T-biotin (1 μM)

The fourth group: G-cold (1 μM)

The four groups of nucleotide analogues were formulated into a mixed solution according to the above concentration and ratio.

4) Phosphate buffered saline (PBS) (Shenggong Bio)

This reagent was used as both antibody ligand buffer and elution reagent.

5) 2 μg/ml Streptavidin-labeled AF532 fluorescence (reagent manufacturer: Thermo Fisher scientific; reagent item number: 434315);

The above-mentioned fluorescently labeled antibodies were all formulated with PBS.

2. Experimental Steps

1) *E. coli* genomic DNA was extracted by referring to the following documents.

So A, Pel J, Rajan S, Marziali A. Efficient genomic DNA extraction for low target concentration bacterial cultures using SCODA DNA extraction technology. Cold Spring Harb Protoc. 2010 (10): pdb. prot5506.

2) Circular single-stranded DNA was prepared by referring to the MGIEasy™ DNA library preparation kit and instructions thereof. The prepared single-stranded circular DNA had been labeled with a barcode sequence.

3) By referring to the instructions of BGISEQ-500 High-throughput Sequencing Kit (SE100), the circular single-stranded DNA was copied through rolling circle to prepare DNA nanospheres. Then, by continuously referring to the instructions of BGISEQ-500 High-throughput Sequencing Kit (SE100), the prepared DNA nanospheres were loaded on sequencing chip.

4) Phosphate buffer solution (Shenggong) was introduced with a flow volume of 300 µl and a flow rate of 200 ul/min into the chip loaded with DNA nanospheres.

5) By referring to the instructions of BGISEQ-500 High-throughput Sequencing Kit (SE100), the sequencing reaction solution was prepared, and the deoxyribonucleotides therein were replaced with the 4 groups of deoxynucleotide analogues 1 or deoxynucleotide analogues 2 in the above experimental materials, the concentrations thereof referred to the experimental materials. The newly prepared sequencing reaction solution was introduced into the chip with a flow volume of 300 µl and a flow rate of 200 ul/min. Incubation was carried out at 55° C. for 1 min. Then, the phosphate buffer (Shenggong) was introduced with a flow volume of 300 µl and a flow rate of 200 ul/min.

6) Signal acquisition buffer (available in the BGISEQ-500 High-throughput Sequencing Kit (SE100)) was introduced into the sequencing chip with a flow volume of 300 µl and a flow rate of 200 ul/min, and then the fluorescence bound on the sequence to be tested was excited by laser (exposure time was 100 ms) and the resultant signal was recorded.

7) Phosphate buffer (Shenggong) was introduced into the sequencing chip with a flow volume of 300 µl and a flow rate of 200 ul/min. Then, streptavidin-labeled AF532 fluorescence (2 µg/ml, Thermo Fisher scientific) was introduced with a flow volume of 150 µl and a flow rate of 150 ul/min, and incubation was carried out at 35° C. for 5 min. Then, phosphate buffer (Shenggong) was introduced with a flow volume of 300 µl and a flow rate of 200 ul/min to remove the free streptavidin-labeled AF532 fluorescence.

8) Signal acquisition buffer was introduced into the sequencing chip with a flow volume of 300 µl and a flow rate of 200 ul/min, and then the fluorescence bound to the sequence to be tested was excited by laser (exposure time was 20 ms) and the resultant signal was recorded.

9) Cleavage reaction solution (available in the BGISEQ-500 High-throughput Sequencing Kit (SE100)) was introduced with a flow volume of 300 µl and a flow rate of 200 ul/min, and incubation was carried out at 57° C. for 1 min.

10) The steps 4 to 9 were cyclically repeated.

11) The fluorescent signal information recorded in each reaction cycle was converted into deoxyribonucleotide information by analysis software.

12) A total of 50 sequencing reaction cycles (for measurement of barcodes) were performed, and the resolution of barcodes was carried out for all read lengths according to the software of the 500 platform, and the resolution rate of each barcode was calculated.

3. Experimental Results

According to the analysis of barcode sequence analysis software, the barcode resolution efficiency was 83.6%.

According to the 50 sequencing reaction cycles, the analysis showed that the mapping rate was 67% and the error rate was 2%.

Figure 3:
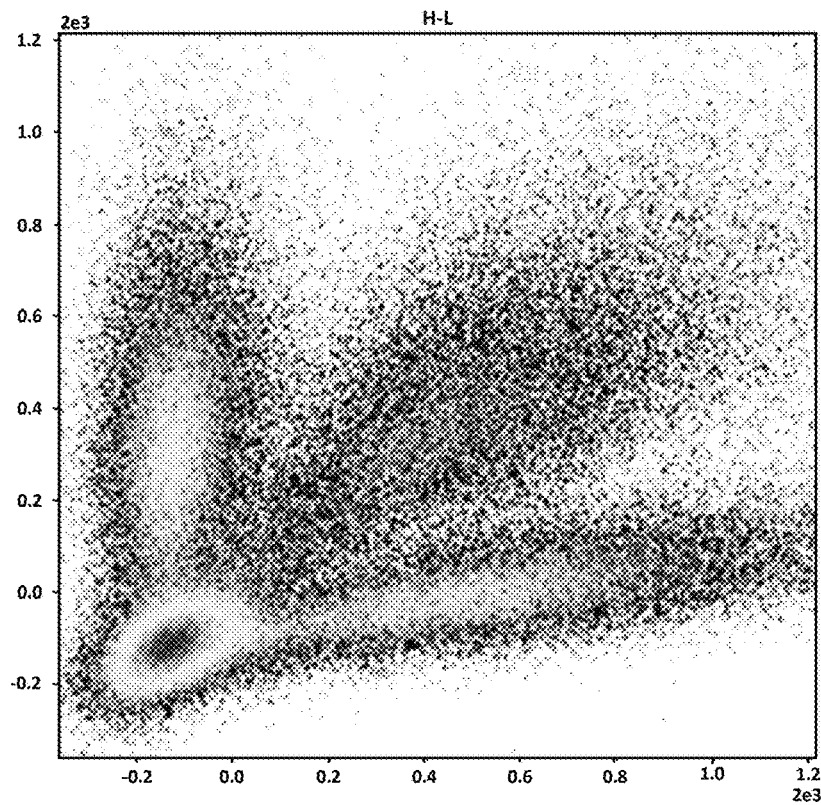
FIG. 3 shows a signal extraction diagram of the $1^{st}$ base during the sequencing of *E. coli* barcode sequence in Example 2.

FIG. 3 was a signal extraction diagram of the 1$^{st}$ base of the sequence to be tested. From the diagram, it could be seen that 4 kinds of deoxyribonucleotides were divided into 4 signal groups according to the detection rules. The lower left corner was the G base signal group; the horizontal signal arm was the A base signal group; the vertical signal arm was the T base signal group; and the signal arm between the A and T signal arms was the C base signal group.

Figure 4:
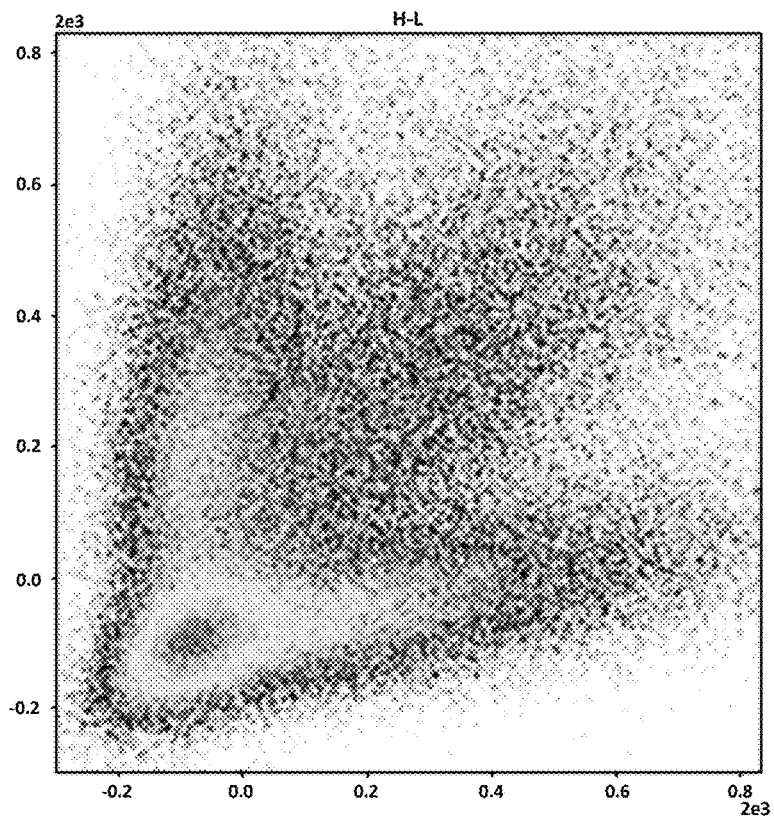
FIG. 4 shows a signal extraction diagram of the $50^{th}$ base during the sequencing of *E. coli* barcode sequence in Example 2.

FIG. 4 was a signal extraction diagram of the 50$^{th}$ base of the barcode sequence to be tested, and the differentiation of signal arms was identical to that of the signal extraction diagram of the 1$^{st}$ base.

Figure 6:
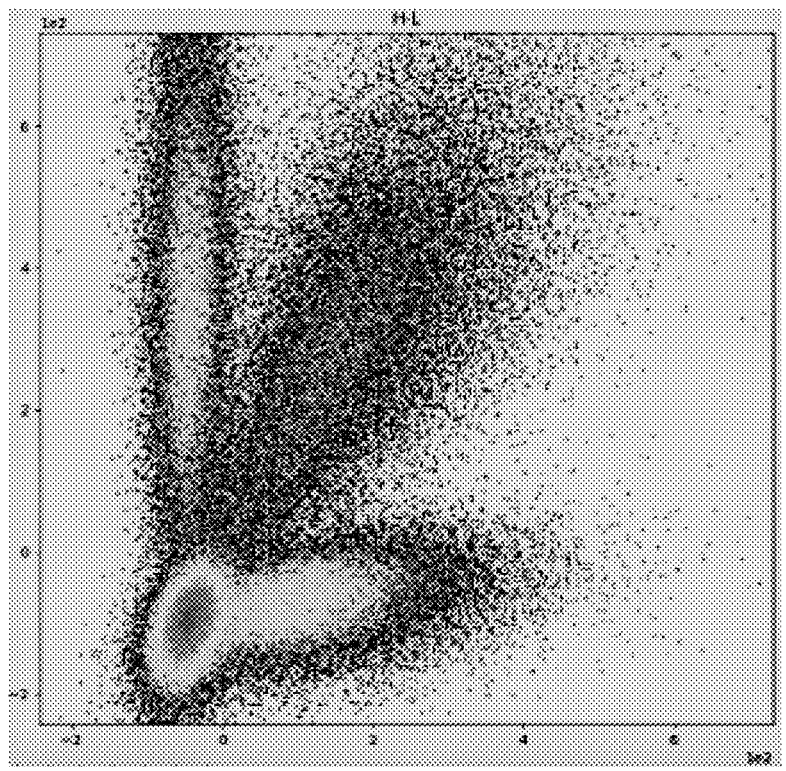
FIG. 6 shows a signal extraction diagram of the $1^{st}$ base during the experiment without adding an unlabeled nucleotide in Example 2.

FIG. 6 was a diagram of signal extraction for the 1$^{st}$ base in the experiment without adding an unlabeled nucleotide, and the differentiation of signal arms was identical to that of the signal extraction diagram of the aforementioned experiment with adding unlabeled nucleotides.

What is claimed is:

1. A method for determining a sequence of a target polynucleotide, which comprises:
   (a) providing a target polynucleotide,
   (b) contacting the target polynucleotide with a primer so that the primer hybridizes to the target polynucleotide, thereby forming a partial duplex of the target polynucleotide and the primer,
   (c) contacting the partial duplex with a polymerase and nucleotides under a condition that allows the polymerase to carry out a nucleotide polymerization reaction, so that a nucleotide is incorporated into the primer, wherein the nucleotides comprise the followings: a first nucleotide, a second nucleotide, a third nucleotide and a fourth nucleotide, wherein
   the first nucleotide comprises a first nucleotide labeled with a first label and an unlabeled first nucleotide, wherein the first nucleotide labeled with the first label and the unlabeled first nucleotide have a ratio of 4:1 to 3:2;
   the second nucleotide comprises a second nucleotide labeled with a second label and an unlabeled second nucleotide, wherein the second nucleotide labeled with the second label and the unlabeled second nucleotide have a ratio of 4:1 to 3:2;
   the third nucleotide comprises a third nucleotide labeled with the first label and a third nucleotide labeled with the second label, and the fourth nucleotide comprises an unlabeled fourth nucleotide,
   wherein each nucleotide has a ribose or deoxyribose moiety that contains a protecting group attached thereto via a 2' or 3' oxygen atom,
   (d) detecting the presence of the first label on the partial duplex of the step (c),
   (e) detecting the presence of the second label on the partial duplex of the step (c),
   (f) optionally removing the protecting group and the label on the nucleotide incorporated in the partial duplex of the step (c),
   (g) optionally repeating the steps (c) to (f) one or more times to obtain sequence information of the target polynucleotide,
   wherein the presence of the first label and the second label is detected by the same luminescence signal.

2. The method according to claim 1, wherein (i) the first label is a luminescent label, and the step (d) comprises detecting the presence of the luminescent label on the partial duplex of the step (c); or, (ii) the first label is not a luminescent label, and the step (d) comprises contacting the partial duplex of the step (c) with a ligand that is labeled with a luminescent label and specifically binds to the first label, and then detecting the presence of the luminescent label on the partial duplex, and optionally, removing the ligand from the partial duplex.

3. The method according to claim 2, wherein the step (e) comprises contacting the partial duplex of the step (c) with a ligand that is labeled with a luminescent label and specifically binds to the second label, and then detecting the presence of the luminescent label on the partial duplex.

4. The method according to claim 3, wherein the step (e) is performed after the step (d).

5. The method according to claim 3, wherein the luminescent label detected in step (d) and the luminescent label detected in step (e) are the same luminescent label.

6. The method according to claim 5, wherein the luminescent label is a fluorescent label.

7. The method according to claim 5, wherein the luminescent label is a fluorophore.

8. The method according to claim 5, wherein the luminescent label is selected from the group consisting of coumarin, an Alexa Fluor fluorescent dye, 4,4-difluoro-4-bora-3a,4a-diaza-s-indacene (Bodipy), fluorescein, tetramethylrhodamine, Phenoxazine, acridine, Cyanine5 (Cy5) fluorescent dye, Cyanine3 (Cy3) fluorescent dye, and sulforhodamine 101 acid chloride (Texas red) fluorescent dye.

9. The method according to claim 8, wherein the luminescent label is an Alexa Fluor fluorescent dye, and wherein the Alexa Fluor fluorescent dye is Alexa Fluor 532 (AF532).

* * * * *